May 17, 1960 F. MEILLAND Plant Pat. 1,943
ROSE PLANT
Filed Feb. 16, 1959
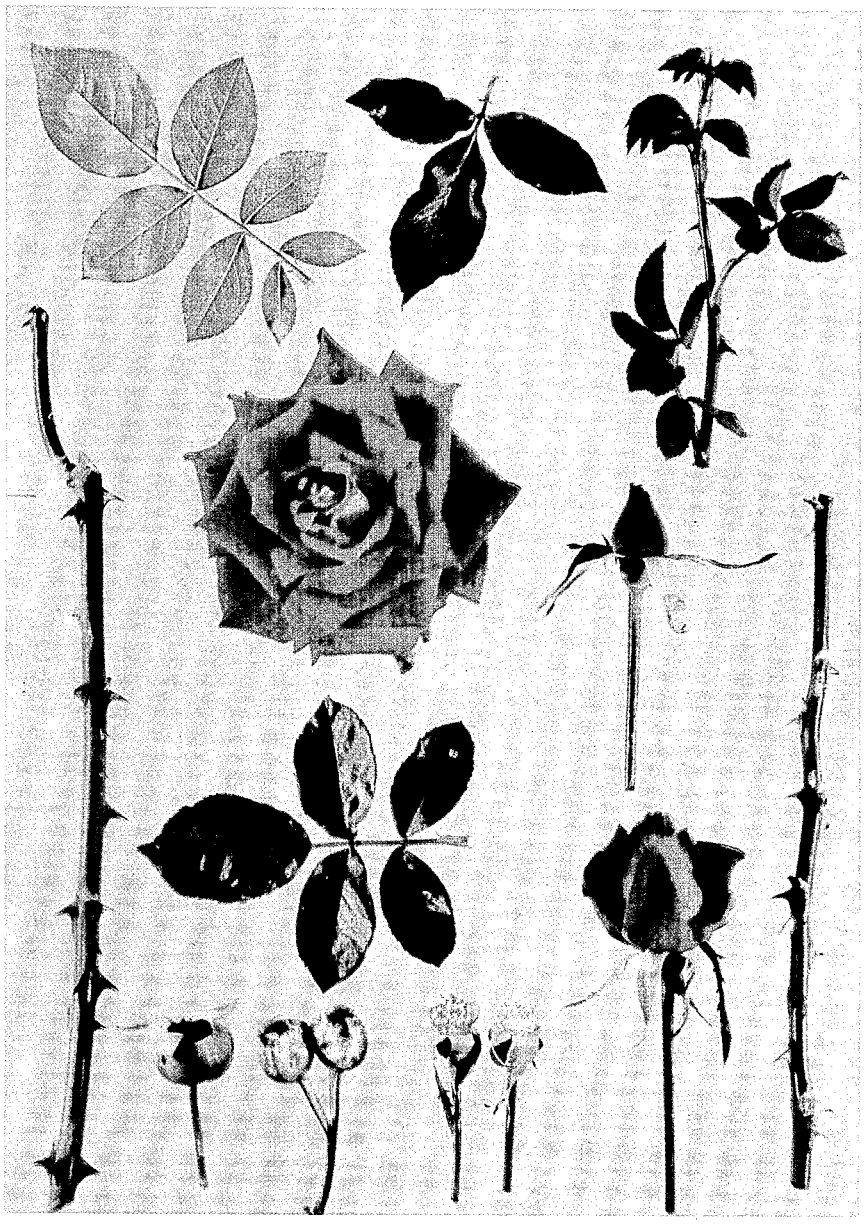
INVENTOR
Francis Meilland Deceased
By: Marie Louise Meilland née Paolino
Legal Representative
BY
Robb & Robb ATTORNEYS United States Patent Office Plant Pat. 1,943
Patented May 17, 1960

1,943

ROSE PLANT

Francis Meilland, deceased, late of Cap d'Antibes, Alpes Maritimes, France, by Marie Louise Meilland, née Paolino, legal representative, Cap d'Antibes, France, assignor to The Conard-Pyle Company, West Grove, Pa., a corporation of Pennsylvania Application February 16, 1959, Serial No. 793,654

Claims priority, application France June 5, 1958

1 Claim. (Cl. 47—61)

The present invention relates to a new and distinct variety of rose plant of the hybrid tea class, which was originated by the applicant by crossing an unnamed and unpatented seedling of "Independence"—known in Germany as "Kordes' Sondermeldung" (U.S. Plant Patent No. 1,036) × "Happiness"—known in France as "Rouge Meilland" (U.S. Plant Patent No. 911), with an unnamed and unpatented seedling of "Peace" (U.S. Plant Patent No. 591) × "Happiness."

The primary objective of this series of breedings was to produce a new rose variety combining the flower color tones of "Independence" with the flower form of "Happiness" and the vigorous plant habit of "Peace." This objective was achieved, along with other desirable improvements, as evidenced by the following characteristics which are outstanding in the new variety and which distinguish it from its parents as well as from all other varieties of which the applicant was aware:

(1) A vigorous habit of growth;

(2) Long-lasting, double, well-formed blooms having excellent color retention which makes them of special value to the cut flower trade; and (3) A Rose Red general color tonality of the blooms which is distinguished by becoming a more intense, glowing and luminous tone under artificial light.

Asexual reproduction of the new variety by budding, as performed in France and at West Grove, Pennsylvania, U.S.A., shows that the foregoing characteristics and distinctions come true to form and are established and transmitted through succeeding propagations.

The accompanying drawing shows typical speciments of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Color Chart of the Royal Horticultural Society, except where general color terms of ordinary dictionary significance are obvious:

Type: Hardy; bush; outdoor; seedling; for cut flowers and for garden decoration.

Class: Hybrid tea.

Breeding: Seedling.

*Seed parent.*—An unnamed seedling of "Independence" × "Happiness."

*Pollen parent.*—An unnamed seedling of "Peace" × "Happiness."

Propagation: Holds its distinguishing characteristics through succeeding propagations by budding.

*Flower*

Locality where grown and observed: West Grove, Pennsylvania, U.S.A.

Flowers borne: Singly to stem; on stems of normal strength and from medium length to long.

Quantity of bloom: Abundant, outdoors.

Continuity: Continuous.

Fragrance: Slight. Nature—tea.

Bud:

*Peduncle.*—Medium length; medium caliper; erect; stiff; medium rough; with medium number of brown hairs. Color—Lettuce Green, Plate 861/3, overlaid with Garnet Brown, Plate 00918/2.

*Before calyx breaks.*—Size—medium. Form—short; pointed; with a conspicuous neck; with foliaceous appendages on the surface of the bud; with foliaceous parts extending beyond the tip of the bud equal to ¼ or more of its length.

*As calyx breaks.*—Color—Maroon, Plate 1030.

*As first petal opens.*—Size—medium large. Form—ovoid. Color: outside—Tyrian Purple, Plate 727, with irregular markings of Beetroot Purple, Plate 830 over the upper half of the petal, shading to Chrysanthemum Crimson, Pate 824/2; inside—Iridescent Rose Red, Plate 724.

*Opening.*—Opens up well.

Bloom:

*Size (when fully open).*—Medium large; from 4 inches to 4½ inches.

*Petalage.*—Very double; from 50 to 60 petals; arranged regularly.

*Form.*—High-centered at first, but becoming cupped; petals being at first loosely rolled outward and remaining loosely rolled outward at maturity.

Petals: Medium leathery; with inside satiny and outside shiny.

*Shape.*—Outer—roundly obovate. Intermediate—roundly obovate. Inner—generally ovate.

This description of a newly opened flower was made from a rose grown outdoors in the month of July at West Grove, Pennsylvania, U.S.A.:

*Color.*—Outer petal: outside surface—Tyrian Purple, Plate 727, shading to Tyrian Rose, Plate 24, with point of attachment Primrose Yellow, Plate 601; inside surface—Rose Red, Plate 724, tinted with Rose Red, Plate 724/1 at basal margin, with point of attachment Sulphur Yellow, Plate 1. Intermediate petal: outside surface—Tyrian Purple, Plate 727/1 at outer margin, shading to Tyrian Rose, Plate 24 and to Cardinal Red, Plate 822/3 over lower half of petal, with point of attachment Primrose Yellow, Plate 601; inside surface—Rose Red, Plate 724 over upper half of petal, shading to Crimson, Plate 22, with basal area surrounding point of attachment Sulphur Yellow, Plate 1. Inner petal: outside surface—Ruby Red, Plate 827/2 at outer margin, grading to Cherry, Plate 722/3, veined with Primrose Yellow, Plate 601 to the point of attachment; inside surface—a velvety Rose Red, Plate 724, with point of attachment Primrose Yellow, Plate 601.

This description was made from a rose that was open for 3 days outdoors in the month of July at West Grove, Pennsylvania, U.S.A.:

*Color.*—Outer petal: outside surface—Rose Bengal, Plate 25/1, shading to Rose Red, Plate 724/3, with point of attachment Dresden Yellow, Plate 62/2; inside surface—Iridescent Rose Red, Plate 724, grading to Iridescent Rose Red, Plate 724/2, with area surrounding point of attachment Primrose Yellow, Plate 601/1. Inner petal: outside surface—China Rose, Plate 024, grading to Cherry, Plate 722/3, sometimes streaked with Naples Yellow, Plate 403/2, with point of attachment Dresden Yellow, Plate 62/1; inside surface—Rose Red, Plate 724/1, grading to Cherry, Plate 722/2, with point of attachment Primrose Yellow, Plate 601/1.

*General color effect.*—Newly opened flower—Rose Red, Plate 724. 3-days open—Rose Red, Plate 724.

*Behavior.*—Drop off cleanly.

*Flower longevity.*—On bush in garden—4 days in August. Cut roses grown outdoors and kept at living-room temperatures—5 days in August.

*Reproductive organs*

Stamens: Many; arranged regularly about pistils.

Filaments: Many—most with anthers; medium length. Color—Scarlet, Plate 19/1, with base Primrose Yellow, Plate 601.

Anthers: All open at once; medium size; occasionally an anther fused with a petaloid. Color—Primrose Yellow, Plate 601.

Pollen: Moderate abundance. Color—gold.

Pistils: Medium number.

Styles: Uneven; medium length; thin caliper; bunched.

Stigma: Color—white.

Ovaries: All enclosed in receptacle.

Hips: None observed.

Sepals: Permanent; medium length; straight.

Seeds: None observed.

*Plant*

Foliage:

*Leaves.*—Compound of 3, mostly 5, and 7 leaflets; abundant; medium size; leathery.

*Leaflets.*—Shape—oval, with apex acuminate. Base—obtuse. Margin—simply serrate.

*Color.*—Mature: upper surface—Parsley Green, Plate 00962; under surface—Sage Green, Plate 000861/1. Young: upper surface—slightly darker than Maroon, Plate 1030; under surface—lighter than Maroon, Plate 1030/3.

*Rachis (the supporting stem of the compound leaf).*—Medium caliper. Upper side—grooved; hairy. Under side—sparsely prickly.

*Stipules.*—Medium length; moderately narrow; with points of medium length turning out at an angle of 45°.

*Disease resistance.*—Comparable to that of the average variety grown under the same cultural conditions at West Grove, Pennsylvania, U.S.A.

Growth:

*Habit.*—Bushy; upright; much-branched.

*Growth.*—Vigorous.

*Canes.*—Medium caliper.

*Main stems.*—Bright. Color—Fern Green, Plate 0862. Prickles—several; color—Garnet Brown, Plate 00918/3. Hairs—none.

*Branches.*—Bright. Color—Fern Green, Plate 0862. Prickles—several; color—Rose Opal, Plate 022/2, overlaying Sap Green, Plate 62/2. Hairs—none.

*New shoots.*—Dull. Color—Fern Green, Plate 0862/1, overlaid with Garnet Brown, Plate 00918/2 towards the bud. Prickles—several; color—Maroon, Plate 1030/3. Hairs—none.

What is claimed is:

A new and distinct variety of rose plant of the hybrid tea class, substantially as herein shown and described, characterized particularly as to novelty by the unique combination of a vigorous habit of growth, long-lasting, double, well-formed blooms having excellent color retention which makes them of special value to the cut flower trade, and a distinctive Rose Red general color tonality of the blooms which becomes more intense and luminous under artificial light.

No references cited.